United States Patent [19]
Cornell

[11] Patent Number: 5,548,095
[45] Date of Patent: Aug. 20, 1996

[54] ELECTRICAL BIO-HAZARDOUS NEEDLE DESTROYER WITH A SPIRAL ELECTRODE

[76] Inventor: Edward C. Cornell, 2518 Ridgeland Ave., Waukegan, Ill. 60085-2561

[21] Appl. No.: 502,969

[22] Filed: Jul. 17, 1995

[51] Int. Cl.[6] .......................... B23K 11/22; A61G 12/00; A61L 11/00
[52] U.S. Cl. ................................................ 219/68
[58] Field of Search ................................. 219/68

[56] References Cited

U.S. PATENT DOCUMENTS

| | | | |
|---|---|---|---|
| 4,628,169 | 12/1986 | Ch'ing-Lung | 219/68 |
| 4,877,934 | 10/1989 | Spinello | 219/68 |
| 4,961,541 | 10/1990 | Hashimoto | 219/68 |
| 4,965,426 | 10/1990 | Colombo | 219/68 |
| 5,138,124 | 8/1992 | Kirk et al. | 219/68 |
| 5,212,362 | 5/1993 | Burden et al. | 219/68 |
| 5,268,549 | 12/1993 | Butler | 219/68 |
| 5,288,964 | 2/1994 | Walker et al. | 219/68 |
| 5,300,752 | 4/1994 | Elmerick et al. | 219/68 |
| 5,336,862 | 8/1994 | Yelvington | 219/68 |
| 5,365,029 | 11/1994 | Makihara | 219/68 |
| 5,468,928 | 11/1995 | Yelvington | 219/68 |

*Primary Examiner*—Geoffrey S. Evans
*Attorney, Agent, or Firm*—McCaleb, Lucas & Brugman

[57] ABSTRACT

Apparatus for destroying bio-hazardous sharp metallic instruments or "sharps" typified by hypodermic needles, hemodialysis fistula and the like wherein a stationary electrified anode is in circuit making engagement with the metallic instrument to be destroyed and the later establishes short circuit engagement with a moveable grounding electrode comprising a rotatably driven annulus or spiral wheel ramp moveable across the an outer end and progressively along the lengthwise axis of the instrument such that a majority of the instrument is burned away and volatilized by short circuit current flow between the metallic instrument and the grounding electrode.

13 Claims, 6 Drawing Sheets

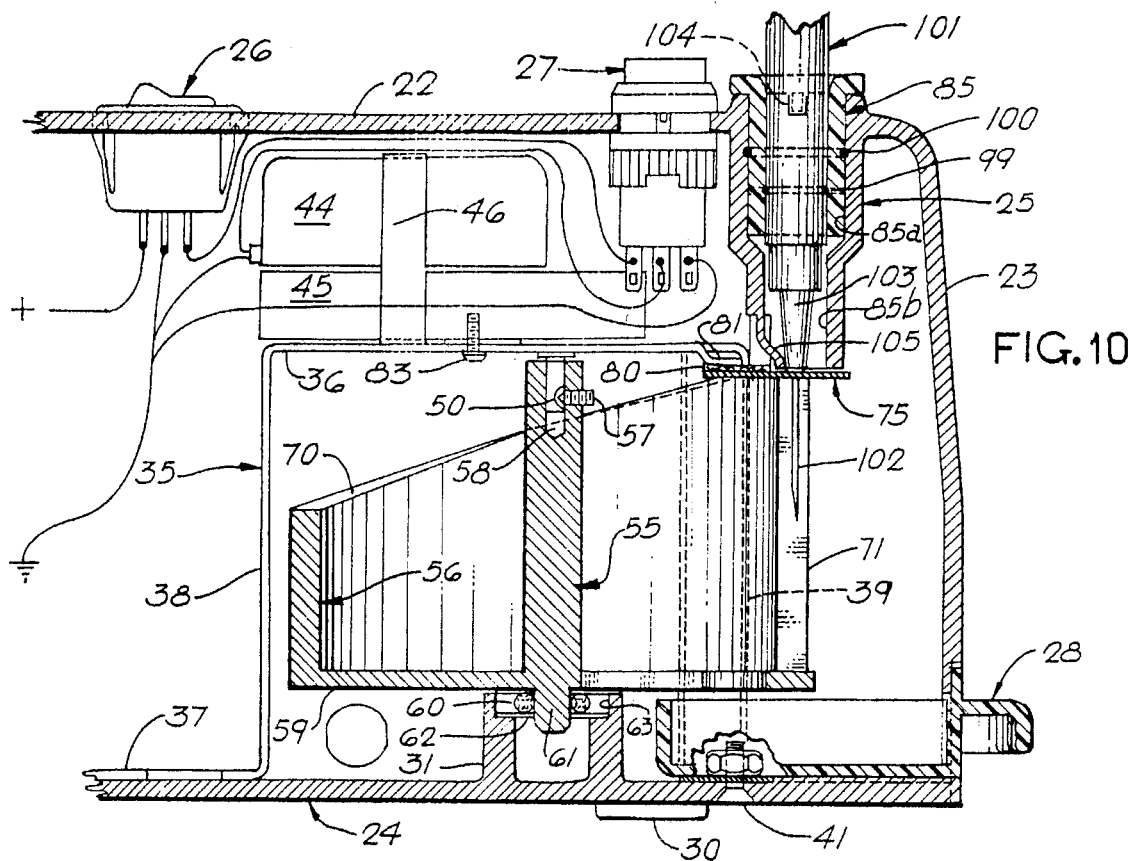
FIG. 10
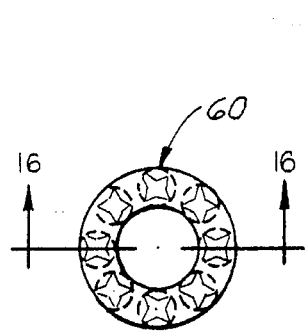
FIG. 15
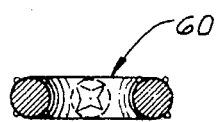
FIG. 16
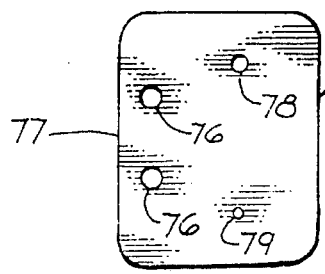
FIG. 11
FIG. 12
FIG. 13
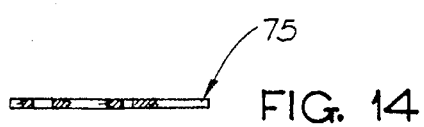
FIG. 14

ELECTRICAL BIO-HAZARDOUS NEEDLE DESTROYER WITH A SPIRAL ELECTRODE

This invention relates to devices for destroying and sterilizing hypodermic syringe needles, hemodialysis fistulae and like "sharp" medical instruments and is more particularly directed to devices employing electrical energy to incinerate and sterilize contaminated or bio-hazardous sharp medical instruments.

BACKGROUND OF THE INVENTION

The use of throw-away hypodermic needles and syringes has become common practice in modern day health care facilities, primarily because the pre-packaged syringes and needles are reliably sterile, convenient to use and eliminate the relatively hazardous and difficult task of sterilizing needles and syringes for re-use.

Despite the apparent desirability and convenience of such throwaway devices, safe disposal of used contaminated needles and syringes presents major economic and safety problems. Incineration of used syringes and needles immediately after use is obviously desirable, but not easily achieved. Bulk disposal of accumulated needle/syringes either by burning, burial or other means is not only expensive, but unsafe, particularly where contaminating substances remain present in the hollow hypodermic needles and syringe bodies. Mechanical severing or breakage of the needles while avoiding their immediate reuse fails to eliminate hazardous and dangerous contaminating fluids and residue whereby accidental engagement of a sharp contaminated needle part becomes a realistic hazard.

It is well known that electrical metal conductors having a relatively low volume to surface area, may be incinerated by electrical resistance heating if subjected to heavy electrical currents even for short time periods. Hollow metal syringe needles and/or dialysis fistulae are good examples of such conductors, and thus are ready candidates for destruction by electrical incineration.

Electrical needle destruction devices employing the incineration effect are known in the prior art as exemplified by U.S. Pat. No. 4,628,169, for example, wherein an end portion of a needle held in a syringe is inserted between a pair of stationary electrodes causing a short circuit to melt the outer end of the needle, leaving an extensive portion of the needle on the needle head. Separator means are provided for detaching the needle head from the syringe.

In a later development set out in U.S. Pat. No. 4,877,934, a syringe held needle is inserted into a slide track to engage a pair of vertically spaced electrodes. The lower electrode angularly converges with the upper electrode and engages the lower end of the needle. By manually moving the needle and syringe toward the inclined electrode, the needle is progressively burned away and disintegrated.

In a more recent U.S. Pat. No. 5,212,362, a needle destroyer employing electrical incineration is set out in which a syringe held needle is inserted into a socket in a housing so that the needle engages a stationary grounding electrode. An electrically active electrode is then pivotally moved onto the needle creating an arc to progressively volatilize or disintegrate the needle.

While the prior art exemplified by the above noted patents provide needle destroying devices designed for on sight use, the use of manually controlled destruction cycles and needle or electrode movements does not ordinarily provide sufficient heating of the needle away from the immediate severance zone to sterilize the needle or syringe of possible bio-hazardous liquids and residue.

BRIEF SUMMARY OF THE INVENTION

The needle destroyer apparatus of this invention is embodied in a portable unit for on sight use immediately after use of a sharp instrument, if possible, and is operable to totally disintegrate or vaporize "sharps", such as hypodermic needles, dialysis needles and like hazardous metallic instruments. The needle destroyer hereof comprises an insulated protective outer housing enclosing an electrically energized plate anode conductor aligned with an externally accessible socket receptacle for the insertion of a syringe and needle combination or a dialysis fistula, for instance, so that the needle or fistula passes through an opening in and makes circuit engagement with the plate anode. A rotatable, motor-driven annular wheel electrode having a vertically spiral ramp is connected to ground and is adapted to engage and move over the lower end of a needle portion extending through the plate anode thereby establishing a short circuit arc and resistive generated heat source to destroy the adjacent end of the needle. In order to completely consume the needle, the inclined, spiral ramp of the grounded electrode follows the receding needle end as it progressively disintegrated to eventually reach the syringe body and needle head which are thereupon heated at sterilizing temperatures. When the wheel ramp completes it's predetermined rotational time cycle, the motor is automatically shut off and the syringe then may be removed having been sealed off by the needle burning and sterilizing operations. Residue from the burnt needle is collected gravitationally into a removable tray located at the bottom side of the housing.

A primary object of this invention is to provide improved means for minimizing health risks involved in storing, processing and handling contaminated sharp medical instruments.

A further object of this invention is to provide apparatus operable at the point of use to disintegrate and sterilize bio-hazardous sharp medical instruments, such as hypodermic syringes, needles and the like.

A still additional object of this invention is to provide an improved electrical means for volatilizing sharp medical instruments.

The above and further objects, features and advantages of this invention will appear from time to time from the following detailed description of a preferred embodiment thereof, illustrated in the accompanying drawings and representing the best mode presently contemplated for enabling those skilled in the art to make and practice this invention.

IN THE DRAWINGS

FIG. 10 is a partial, enlarged, sectional view corresponding to the right hand portion of FIG. 2 showing particulars of the wheel ramp electrode and related parts;

FIG. 11 is a top plan view of an insulator associated with the plate anode;

FIG. 12 is a cross sectional view of the insulator seen in FIG. 11, taken substantially along vantage line 12—12 of FIG. 11;

FIG. 13 is a top plan view of the plate anode shown in FIG. 10;

FIG. 14 is an end elevational view thereof;

FIG. 15 is a top plan view of a bearing assembly associated with the wheel ramp electrode hereof;

FIG. 16 is a sectional view of the bearing assembly seen in FIG. 15, taken substantially along vantage line 16—16 of FIG. 15;

DESCRIPTION OF THE PREFERRED EMBODIMENT

Figure 1:
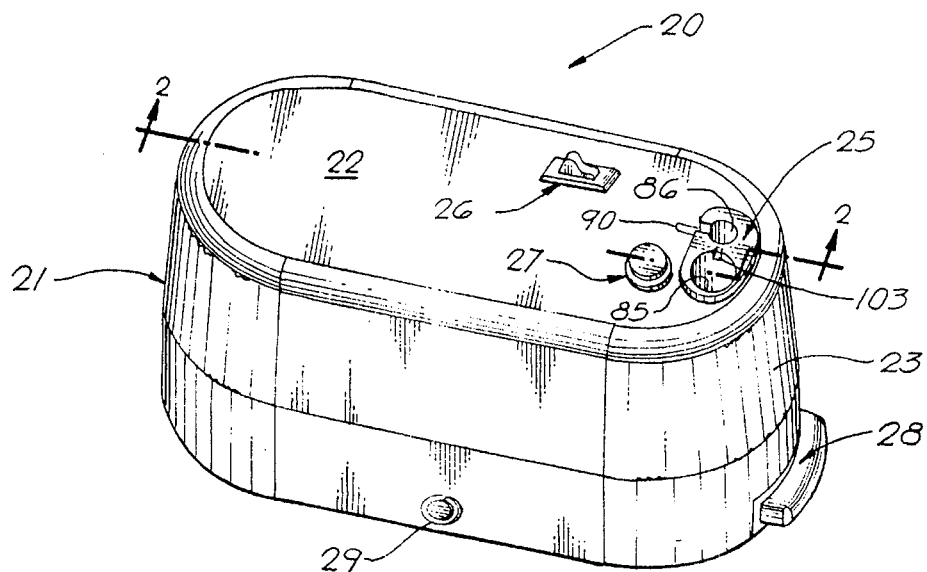
FIG. 1 is a perspective view of a needle destroying apparatus embodying the present invention.
Figure 2:
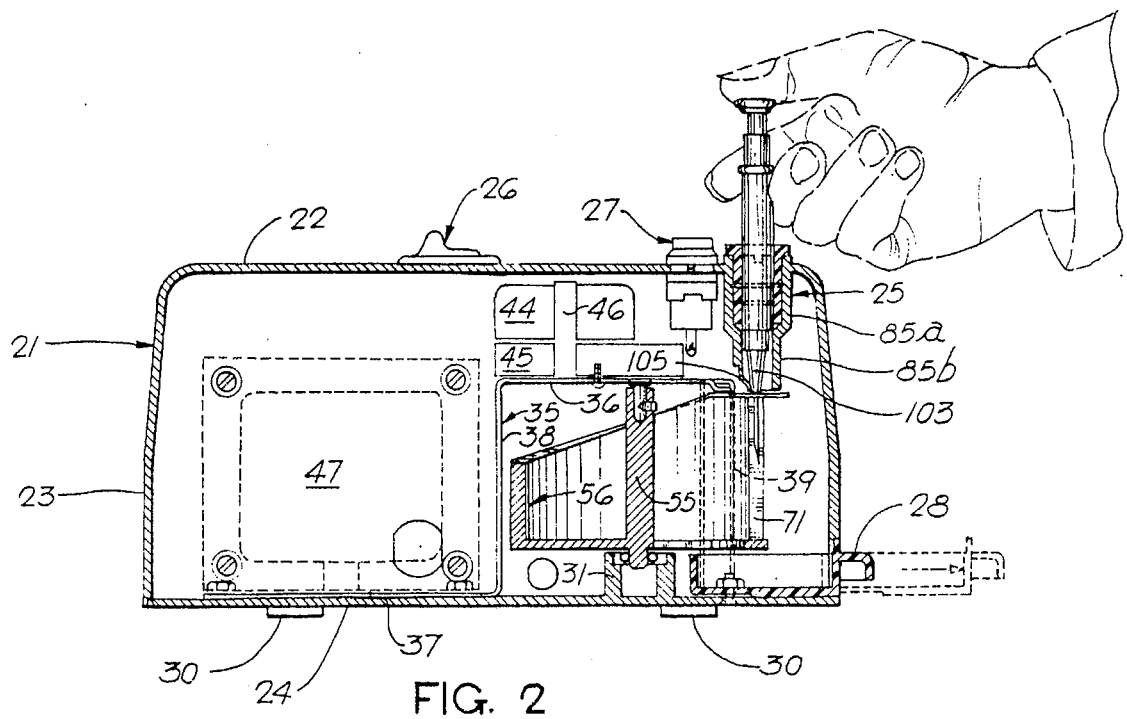
FIG. 2 is a longitudinal cross-sectional view taken substantially along vantage line 2—2 of FIGS. 1 and 5 and looking in the direction of the arrows thereon.

With initial reference to FIG. 1 of the drawings, a needle destroying apparatus according to this invention is indicated generally by numeral 20 thereat as comprising a generally oblong unitary molded housing 21 having a top wall 22, side walls 23 and a detachable bottom wall 24 (see FIG. 2). The housing top wall is provided with a receptacle portion 25 for the inserted reception of hypodermic syringes and hemodialysis fistulae in the particular herein illustrated embodiment as will appear in greater detail hereinafter. In addition the top wall 22 of the housing is fitted with a lighted rocker type on/off switch 26 having a ready light to indicate the operating condition of the unit and a start switch 27. One end of the housing 21 is equipped with a opening for the reception of a slide out drawer or tray 28 for catching disintegrated ashes, parts and debris of destroyed "sharps" in accordance with this invention. A circuit breaker having a reset button 29 for resetting the circuit in the event of electrical overload is accessible at of one side of the housing.

Preferably housing 21 is formed with integral top and side and end walls as a unitary molding of suitable plastic material and more particularly of a fire proof or flame retardant plastic. As noted, bottom wall 24 is separate and removeable from the remainder of the housing and serves as a mounting platform for the internal working elements of the incinerator apparatus. It will be seen from FIGS. 2–4 in particular that the bottom wall 24 is formed with four integral foot pads 30, 30 projecting from the lower face thereof. Additionally, on the inner face of bottom wall 24 a cylindrical boss 31 is provided generally adjacent the end of the apparatus nearest the clean out drawer or tray 28 for purposes which will appear hereinafter.

Mounted within housing 21 is a metal support bracket indicated generally at 35 comprising parallel upper and lower laterally spaced platform portions 36 and 37 respectively, which are laterally offset from one another and are interconnected by a vertical wall 38 aligned substantially on the medial axis of the housing 21. Platform portion 36 is further supported by two vertical leg portions 39, 39 extending downwardly from the outer ends of two divergent arm portions 40 extending from one end of the platform portion 36 adjacent the clean out drawer end of the unit (see FIG. 5). The lower platform portion 37 of the bracket as well as foot portions 41 at the lower ends of the post portions 39 are suitably affixed to the bottom wall 24 of the housing by threaded fasteners 42 (see FIGS. 2 and 5).

Figure 9:
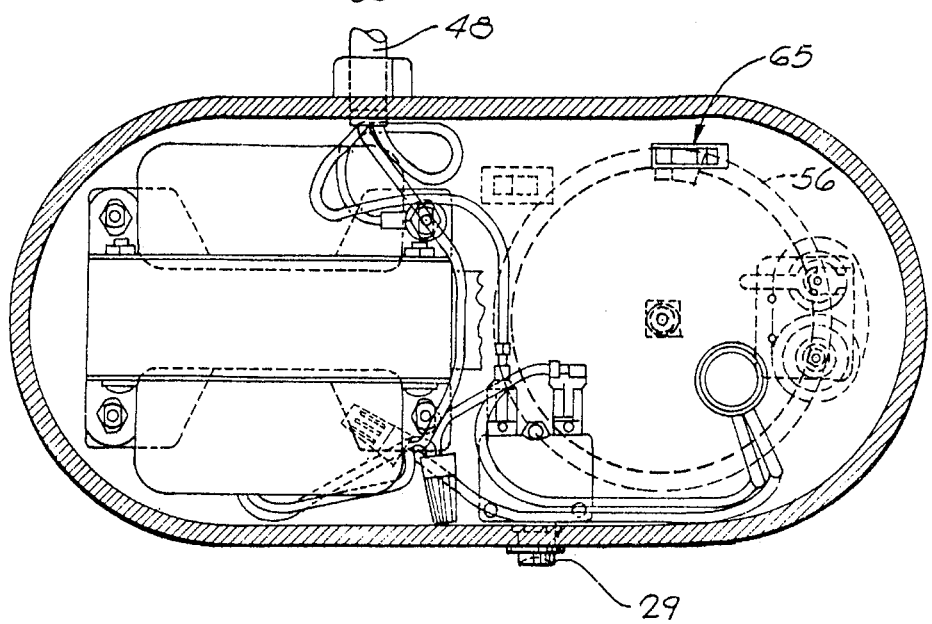
FIG. 9 is another top plan view of the apparatus shown in FIG. 1 with the top wall removed and other removed parts shown in phantom.
Figure 17:
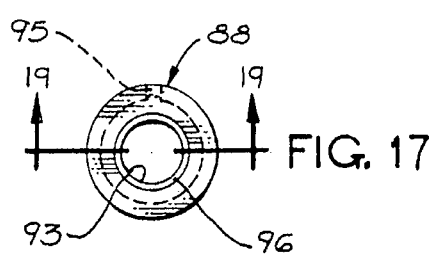
FIG. 17 is a top plan view of a syringe insert used in the apparatus shown in FIG. 1.
Figure 21:
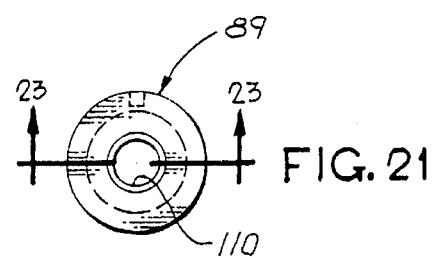
FIG. 21 is a top plan view of another insert useful with the apparatus shown in of FIG. 1.
Figure 18:
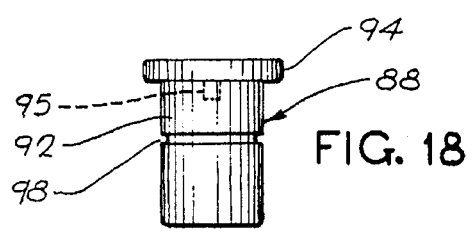
FIG. 18 is a front elevational view thereof.
Figure 22:
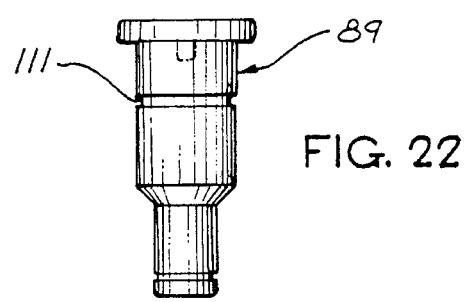
FIG. 22 is a front elevational view thereof.
Figure 19:
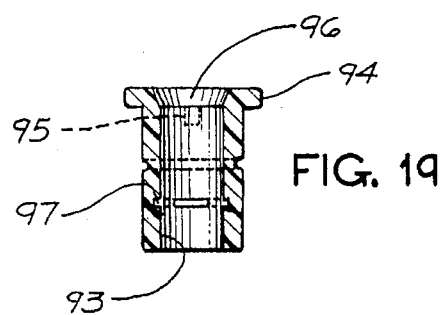
FIG. 19 is a cross-sectional view of the insert shown in FIGS. 17 and 18, taken substantially along vantage line 19—19 of FIG. 17 and looking in the direction of the arrows thereon.
Figure 23:
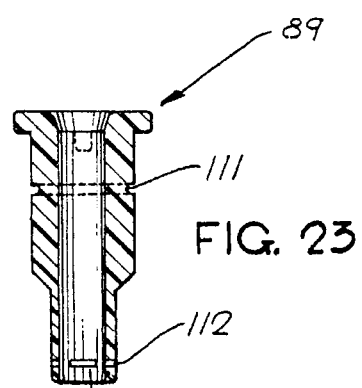
FIG. 23 is a cross-sectional view of the insert seen in FIG. 21, taken substantially along vantage lines 23—23 of FIG. 21 and looking in the direction of the arrows thereon.
Figure 20:
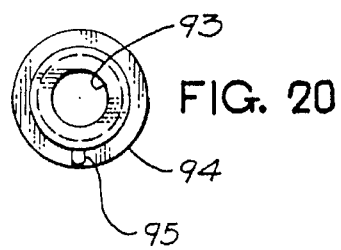
FIG. 20 is a bottom plan view of the insert shown in FIGS. 17–19.
Figure 24:
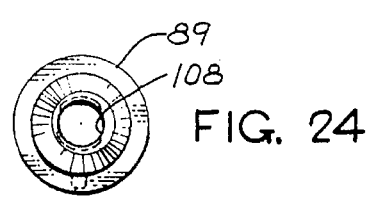
FIG. 24 is a bottom plan view of the insert shown in FIGS. 21–23.

Mounted on top of the platform 36 is an electrical drive motor 44 and gear reducer 45 held by mounting bracket 46 while the lower platform portion 37 supports a step down AC transformer 47 rated at 12 volts, 168 va, supplied by a normal household supply 120 volt, 60 cycle AC over a three wire grounded conductor 48 leading from the housing 21 and equipped with the usual three prong male connector plug 49 as best shown in FIG. 9. Typically motor 44 is a 110 volt, 60 hrz, 6 watt motor and the gear reducer 45 is productive of 18–20 rpm for rotatably driving its output shaft 50 and a central hub post 55 of an annular metal electrode 56. It will be noted from FIG. 10 that a set screw 57 serves to lock the shaft 50 in a coaxial bore 58 at the upper end of the hub post 55 whereby to rotatably drive the electrode 56 in accordance with the rpm's of shaft 50. In order to rotatably support the electrode 56 the bottom end of the hub 55 extends beyond a bottom wall 59 of the electrode and fits coaxially within the cylindrical bearing boss 31 extending upwardly from the housing bottom wall 24. A ball bearing assembly 60 concentrically surrounds the extending hub portion 61 beneath bottom wall 59 of the electrode 56; such bearing assembly 60 resting on top of a plate washer 62 carried in a shouldered counter bore 63 at the upper end of the bearing boss 31.

Figure 7:
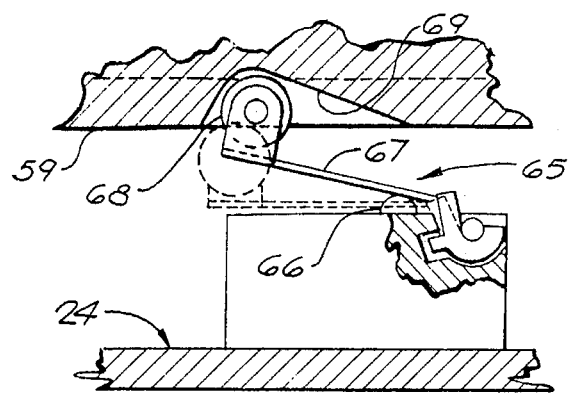
FIG. 7 is an enlarged elevational view with parts in section of a stop switch assembly associated with a wheel ramp electrode of the needle destroyer apparatus hereof.
Figure 8:
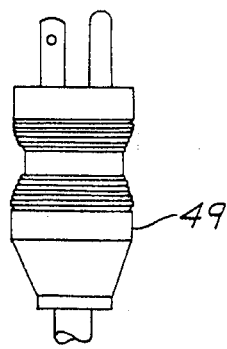
FIG. 8 is a top plan view of the switch assembly shown in FIG. 7.
Figure 8:
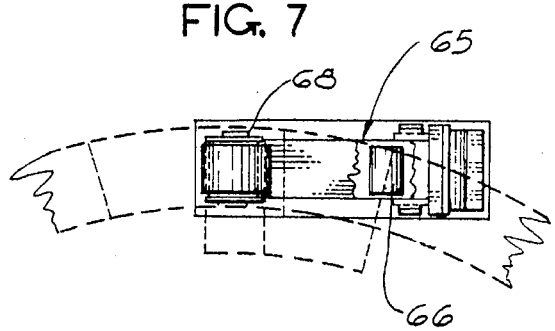

It will be noted from FIGS. 7, 8 and 9 in particular, that a normally open stop switch assembly 65 is mounted between the bottom 59 of the electrode wheel and the bottom wall 24 of the housing. More specifically, switch assembly 65 includes a micro-switch actuator 66, engageable with a pivotal rocker arm 67 having a follower wheel 68 at its outer end for engaging and rolling over the bottom perimeter of the electrode wheel (see FIG. 8). The switch assembly 65 is designed to meter the rotational of movement of the electrode wheel 56 by specifically deenergizing the drive motor 44 after each complete revolution of the annular electrode wheel. In order to accomplish this, the lower perimetel margin of the electrode 56 is provided with a nodal depression 69 (see FIG. 7), which permits the roller 68 to enter the node and move upwardly at a designated location along the rotational path of the electrode wheel. When the arm 67 moves upwardly as indicated in FIG. 7 the micro-switch actuator 66 is biased upwardly to open the switch 65, thereby deenergizing the drive motor and stopping rotational movement of the electrode wheel.

Figure 3:
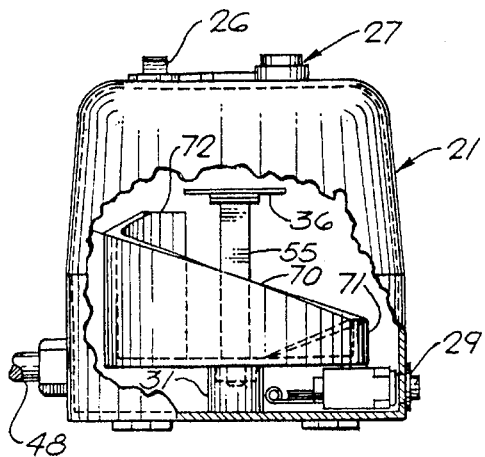
FIG. 3 is a left hand end elevational view of the needle destroyer shown in FIG. 1 with portions of the end wall broken away.
Figure 4:
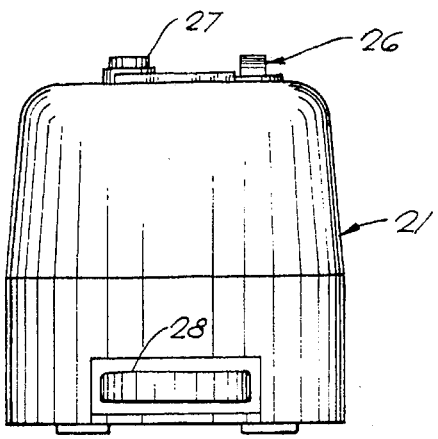
FIG. 4 is a right hand elevational view thereof.

In addition to the features of the annular electrode wheel 56 set forth so far, it will be noted that this annular wheel is particularly distinguished by a inclined spiral ramp defined by upper edge 70 of its side wall 71 (see FIGS. 3 and 10). It will be noted from FIG. 3 that the spiral ramp edge 70 extends from the bottom wall 59 upwardly until it intersects a planar horizontal top edge portion 72 at the upper end thereof which parallels bottom wall 59. The presence of this upper portion 72 permits disintegration of a hypodermic needle, for example, very close to the head of the needle and also permits sterilization heating of the hypodermic syringe.

Figure 5:
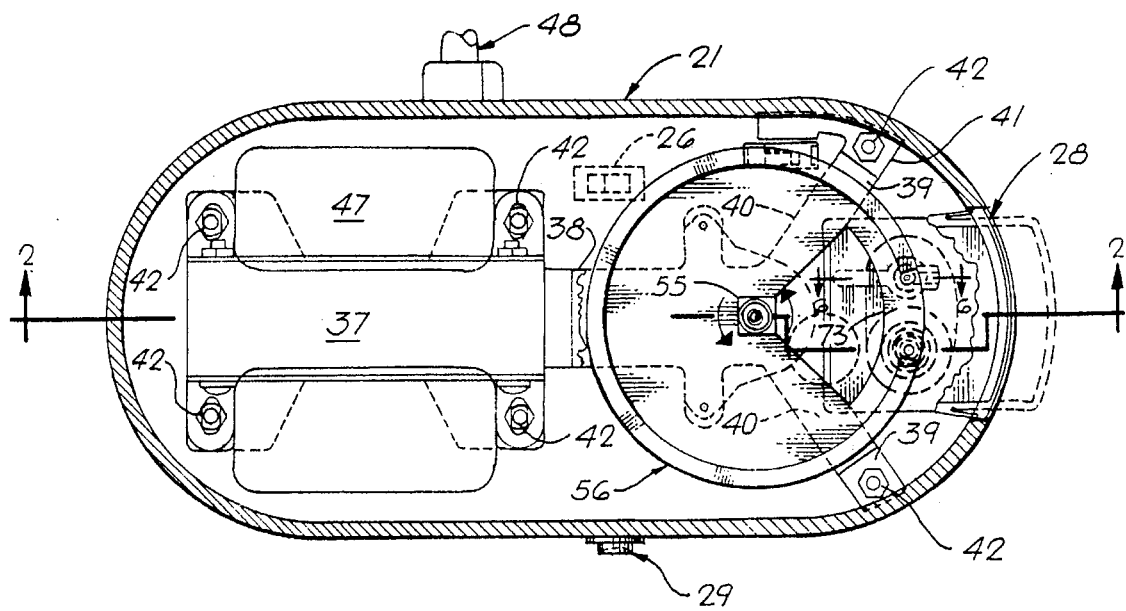
FIG. 5 is a top plan view thereof with top wall removed and portions in phantom to show the internal arrangement of parts.

Beside the unique ramp formation of the electrode wheel it is to be noted that its bottom wall 59 has an arcuate sector cut out 73 (see FIG. 5) extending between the termination of horizontal ramp portion 72 and the initiation of the incline for ramp 70 as best illustrated from FIGS. 3 and 5 of the drawings. This cut out sector registers with the underlying or underdisposed clean out tray 28 when the latter in its housed condition, as shown in FIG. 10. Thus residue, disintegration ash and needle parts from a vaporized needle fall directly into the clean out tray 28, as desired.

It will be understood that the electrode wheel 56 is a negative or grounded electrode coupled to ground. To produce the desired short circuiting disintegration of a needle according to this invention, it is necessary to provide a positively charged anode to act in conjunction with the negative electrode and to establish a short circuit therebetween by the needle sharp to be disintegrated therebetween. To that end, a planar electrode plate 75 is provided, as best illustrated in FIGS. 13–14, comprising a brass or copper plate with a pair of side by side mounting openings 76, 76 adjacent one marginal edge 77 thereof and two different diameter needle receptive openings 78 and 79 in the particular illustrated embodiment hereof. In this latter regard, opening 78 is of substantially larger diameter than that of 79; the latter being receptive of a normal hypodermic needle while opening 78 is of a size to accept a larger standard dialysis needle.

As best seen in FIG. 10 of the drawings, the plate anode 75 is mounted to extend over the upper end of of the electrode wheel, more specifically in parallelism with the upper reaches of the horizontal portion 72 of the ramp. A rectangular insulator plate 80 is disposed between the upper face of the electrode plate 75 and a mounting platform portion 81 of the bracket 35 comprising an offset extension of the right hand bracket platform 36 as shown in FIG. 10 of the drawings. It will be noted from FIG. 11 that the insulator plate 80 has a pair of spaced openings 82 therein which register with opening 76, 76 of the anode plate in assembly and that the anode plate, intervening insulator 80 and the platform portion 81 are interjoined by bolt and nut fasteners, rivets or the like in requisitely insulated fashion from bracket 35 which is at ground potential, while the anode plate is positively charged when energized.

Grounding the electrode wheel is accomplished by a ground screw connection 83 which interjoins the support bracket 35 with the motor mount bracket 44, both of which are grounded.

Referring now to FIGS. 2 and 10, it will be recalled that the housing 21 incorporates a receptacle portion 25 adjacent one end wall thereof; such receptacle 25 comprising a pair of generally cylindrical sockets 85 and 86 (see FIG. 1) which are adapted to receive, align and hold hypodermic syringes and dialysis fistulae, respectively, in operating position for destruction of related needle sharps and similar instruments in the destroyer 20 hereof. As best shown in FIG. 10, socket 85 comprises a cylindrical upper portion 85a and a coaxially aligned lower cylindrical portion 85b of substantially smaller diameter. Socket 85 is receptive of a generally cylindrical insert such as insert 88 illustrated in FIG. 17–20 or a dual diameter insert 89 as illustrated in FIGS. 21–24 for example.

Figure 6:
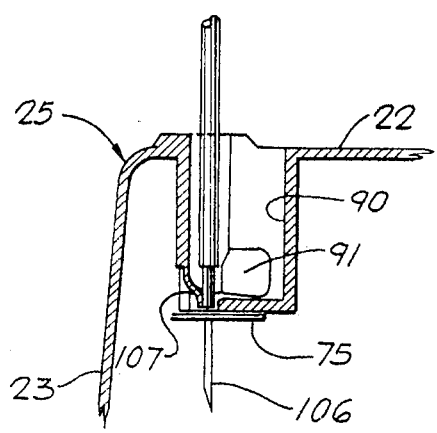
FIG. 6 is an enlarged partial sectional view taken substantially along vantage line 6—6 of FIG. 5, looking in the direction of the arrows thereon.

The receptacle socket 86 on the other hand is directed to the reception of dialysis fistula and the like in which no insert such as 88 or 89 is required due to the fact that socket 86 is formed with a lateral guide slot 90 that receives a wing 91 of the dialysis cannula to guide and maintain the needle in proper position for destruction (see FIG. 6).

With reference to FIGS. 17–20, the insert 88 is a unitary molding of ABS plastic comprising a cylindrical body 92 formed with a coaxial interior cylindrical chamber 93 having an annular cap rim 94 about its upper end. A guide key 95 extends radially from body 92 beneath cap 94 and a chamfered guide 96 is provided around the upper end of chamber 93. Annular kerfs 97 and 98 invade the interior wall of chamber 93 and the exterior wall of body 92 for holding O-ring seals 99 and 100, respectively, (see FIG. 10). In this respect kerf 97 while formed inwardly of the exterior of body 92 cuts through opposite sides of the walls of chamber 93. Thus chordal portions of O-ring 99 extend across opposite sides of chamber 93 to retain the syringe within the insert 88 while O-ring 100 serves to retain the insert 88 in socket 85.

Insert 88 is designed to receive a medium size hypodermic syringe 101 having a sharp needle 102 extending from the lower needle hub 103 thereof. The internal O-ring 99 serves to hold the syringe body in the insert while the latter is held in socket 85 by the exterior O-ring 100 with the guide key 95 engaged with a matching guide 104 at the upper end of socket 85.

It will be understood that the needle 102 of the syringe assembly shown in FIG. 10, extends through the smaller opening 79 in the anode plate 75 and projects beneath the anode for engagement by electrode 56 when the latter is rotatably activated.

In this regard, importantly the receptacle portion 25 of the housing 21, is provided with means for insuring positive contact of the needle sharp with the anode plate. To this end the lower end portion 85a of the socket 85 is formed with an integral spring finger 105 that interferingly engages and presses against one side of needle hub 103 to force the needle 102 positively against one side of the anode plate opening 79 (see FIG. 10). In similar fashion a dialysis needle 106 is biased onto the anode by spring finger 107 formed integrally with socket 86 (see FIG. 6).

Turning to FIGS. 21–24, it will be appreciated that the insert 89, shown thereat, is formed to fit closely within the syringe socket 85, being molded with two cylindrical portions to fit both portions 85a and 85b of socket 85. The major difference between insert 89 and the previously described insert 88, is in the diameter of its internal cylindrical chamber 110 which is much smaller than the corresponding cylindrical chamber 93 of insert 88 and is designed to accommodate small diameter syringes. As shown, annular kerfs 111 and 112 receive O-rings to hold the syringe body in the socket member 85 and retain a syringe within the interior chamber 10. It also will be noted from FIG. 24 especially that the cylindrical chamber 110 is slightly offset from coaxial alignment with the body of insert 89. This is to permit the very small needle associated with a small size syringe, to contact the side of anode opening 79 without extensive bending under the force of spring 105.

It will be recognized from the foregoing that with a hypodermic mounted needle inserted into the insert member 85, as illustrated in FIG. 10, needle 102 thereof is in circuit with the anode plate 75 under the influence of the spring means 105. However, the rotatable electrode 56 in its stop position, as shown in FIG. 10, is out of engagement with the needle. Once the start switch 27 is depressed, motor 44 rotates wheel 56 counter clockwise to bring the ramp 70 thereof into contact with the tip of needle 102 (see FIG.3). Once the needle engages the grounded electrode wheel, short circuit sparking and heating of the needle takes place to burn and disintegrate the needle until the upper portion 72 of the wheel electrode engages the needle holding end of the syringe. When this occurs, the remaining shank of the needle is heated sufficiently to melt the syringe end and seal off the needle hub 103 thereof, as well as the hollow needle shank. When the roller actuated stop switch reaches the depression node 69, motor 44 is deenergized along with the anode and electrode, ending the destruction cycle. A corresponding destruction cycle takes place when a dialysis needle placed in socket 86.

Figure 25:
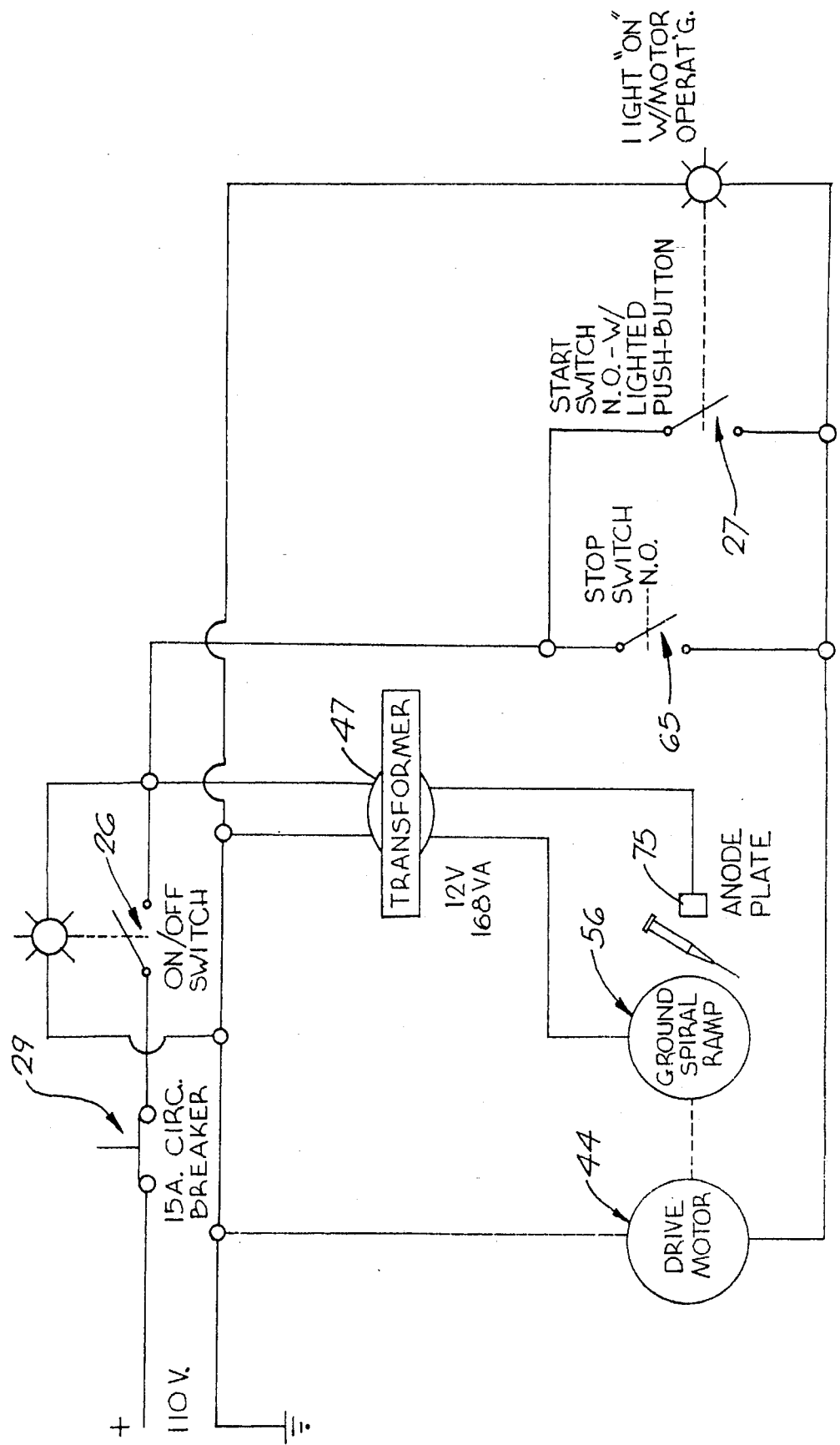
FIG. 25 is a schematic electrical circuit diagram employed in the needle destroying apparatus of FIG. 1.

To briefly understand the electrical control of apparatus 21, reference is made to the schematic circuit set out in FIG. 25. As there shown when the on/off switch 26 is enclosed, the transformer and anode plate are energized and the circuit to the start switch 27 is in stand by condition. Momentary closing of the normally open start switch 27 energizes its associated ready light and the motor 44 to rotate the ramp electrode. As soon as the stop switch 65 has its follower roller out of the node 69, the start switch opens and switch 65 maintains the closed circuit condition until its follower wheel 68 again enters node 69 to disengage the motor 44 and stop movement of the electrode wheel 56 ready for the next destruction cycle.

From the foregoing it is believed that those familiar with the art will readily recognize the improved advancement afforded by this invention and will appreciate that while the same has herein been described in relation to a preferred embodiment thereof, illustrated in the accompanying drawings, such is susceptible to modifications, variations and substitution of equivalents without departing from the spirit and scope of this invention which is intended to be unlimited by the foregoing except as may appear in the following appended claims.

The embodiments of the invention in which an exclusive property or privilege is claimed are defined as follows:

1. Apparatus for destroying bio-haardous instruments having elongated sharp metallic needle portions, comprising:
   a stationary, anode engageable with said needle portion to be destroyed;
   a movable electrode having an annular body formed with an inclined edge defining a spiral ramp with a circular length;
   electrical circuit means for selectively energizing said anode with positive energy and maintaining said electrode at ground potential;
   means for positioning and maintaining said needle portion to be destroyed in circuit engagement with said anode so that said portion is positively charged thereby and extends beyond said anode for engagement by said ramp; and
   means for progressively moving said ramp along the circular length to maintain contact with the outer end of said needle portion and thereby establish short circuit connection between said electrode and anode productive of heat and electrical arcing of sufficient intensity to volatilize and disintegrate the axial needle portion extending between said anod and electrode.

2. The apparatus of claim 1, wherein said anode has at least one opening therethrough for the passage of said needle portion.

3. The apparatus of claim 1, including a molded plastic housing enclosing said anode and electrode, an electrical motor for rotatably driving said electrode, and a stop switch in said circuit means for deenergizing said motor after each revolution of said electrode.

4. The apparatus of claim 3, wherein movement of said ramp is sufficient to insure complete volatalization of said needle portion during a single revolution of said electrode.

5. The apparatus of claim 3, wherein said stop switch is reactive to a pre-selected rotational position of said electrode.

6. The apparatus of claim 5, wherein said pre-selected position is defined by a nodal depression receptive of an actuator for said stop switch.

7. The apparatus of claim 1, and a unitary housing enclosing said anode and electrode and formed with an exteriorly accessible walled socket, adaptor means insertible into said socket for receiving said bio-hazardous instruments having needle portions, and operable to hold said needle portions in circuit making contact with said anode.

8. The apparatus of claim 1 and spring means engageable with said instrument for maintaining the needle portion to be destroyed in circuit making engagement with said anode.

9. The apparatus of claim 1, wherein said anode is a planar metal plate having an opening therethrough for the passage of needle portions to be destroyed.

10. The apparatus of claim 9, wherein said anode has multiple openings therethrough for passage of needle portions of different diameters.

11. The apparatus of claim 1, wherein said circuit means comprises a step-down transformer for low voltage energization of said anode.

12. The apparatus of claim 1, wherein said anode is operationally horizontal, each said needle portion to be destroyed is vertically oriented and passes at right angles through said anode to subtend therebeneath, and said electrode is disposed below said anode to rotate about a vertical axis with the ramp thereof aligned to interferingly engage the outer free end of said needle portion and progress vertically along the longitudinal axis of said needle portion as said needle portion is volatilized and disintegrated.

13. The apparatus of claim 7, wherein said housing is made of molded plastic and said socket includes a flexible finger extension operable to bias said needle portion into circuit making contact with said anode.

* * * * *